United States Patent
Andrews et al.

(10) Patent No.: US 9,643,103 B2
(45) Date of Patent: May 9, 2017

(54) PROCESS FOR PREPARING LIQUID MIXTURES OF KNOWN PH AND SALT CONCENTRATION

(75) Inventors: Richard W. Andrews, Rehoboth, MA (US); John Heden, Hollis, NH (US); Michael Jackson, Woonsocket, RI (US); John Lamoureux, Franklin, MA (US); Guo-Zhong Li, Westborough, MA (US); Barry Sunray, Northborough, MA (US); Thomas E. Wheat, Hopedale, MA (US)

(73) Assignee: Waters Technologies Corporation, Milford, MA (US)

( * ) Notice: Subject to any disclaimer, the term of this patent is extended or adjusted under 35 U.S.C. 154(b) by 766 days.

(21) Appl. No.: 13/695,811

(22) PCT Filed: May 24, 2011

(86) PCT No.: PCT/US2011/037645
§ 371 (c)(1),
(2), (4) Date: Apr. 29, 2013

(87) PCT Pub. No.: WO2011/149872
PCT Pub. Date: Dec. 1, 2011

(65) Prior Publication Data
US 2013/0206666 A1 Aug. 15, 2013

Related U.S. Application Data

(60) Provisional application No. 61/348,280, filed on May 26, 2010.

(51) Int. Cl.
*B01F 15/04* (2006.01)
*G05D 11/02* (2006.01)
(Continued)

(52) U.S. Cl.
CPC ........... *B01D 15/16* (2013.01); *B01D 15/168* (2013.01); *B01F 15/04* (2013.01); *G01N 30/34* (2013.01); *G05D 11/02* (2013.01)

(58) Field of Classification Search
CPC ...... B01D 15/16; B01D 15/06; B01D 15/166; B01D 15/168; B01D 17/12; G01N 30/34;
(Continued)

(56) References Cited

U.S. PATENT DOCUMENTS 6,221,250 B1   4/2001   Stafstrom
6,299,767 B1 * 10/2001   Dourdeville ......... B01D 15/166
                                                     210/101

(Continued)

OTHER PUBLICATIONS

Publication: "Microfluidic Temperature Gradient Focusing", David Ross et al, Analytical Chemistry, vol. 74, Published 2002, pp. 2556-2564.*

(Continued)

*Primary Examiner* — Joseph Drodge
(74) *Attorney, Agent, or Firm* — Waters Technologies Corporation

(57) ABSTRACT

A method of preparing a liquid mixture for use in a liquid chromatography system is provided. The mixture comprises one or more acids, one or more bases, one or more salts, and one or more solvents, and the method comprises the steps of: i) calculating pH and/or salt concentration at a particular time t from a user-determined gradient function; and ii) based on the values obtained in step (i), calculating percent acid, percent base, percent salt and percent solvent in the liquid mixture at time t. A liquid chromatography system incorporating such method is also provided.

6 Claims, 3 Drawing Sheets

(51) Int. Cl.
*B01D 15/16* (2006.01)
*G01N 30/34* (2006.01)

(58) Field of Classification Search
CPC .. G01N 2030/342; G05D 11/02; G05D 11/08; G05D 11/135; G05D 11/138; G05D 11/139; B01F 15/04; B01F 15/0404; B01F 15/0412; B01F 15/0441; C02F 1/68; C02F 1/685; C02F 1/686
USPC ............. 210/198.2, 656, 739; 252/364; 366/152.1, 160.1, 162.1
See application file for complete search history.

(56) References Cited

U.S. PATENT DOCUMENTS

| | | |
|---|---|---|
| 2002/0009388 A1 | 1/2002 | Lombardo et al. |
| 2005/0247625 A1* | 11/2005 | Liu ................. B01D 15/166 210/635 |
| 2008/0053830 A1 | 3/2008 | Tsonev et al. |
| 2008/0279038 A1* | 11/2008 | Bellafiore et al. ......... 366/152.4 |

OTHER PUBLICATIONS

PCT International Search Report and Written Opinion for PCT/US11/37645, Forms PCT/ISA/220, 210 and 237, mailing date of Aug. 6, 2011, 8 pages.

* cited by examiner

PROCESS FOR PREPARING LIQUID MIXTURES OF KNOWN PH AND SALT CONCENTRATION

CROSS-REFERENCE TO RELATED APPLICATIONS

This application claims priority to U.S. Provisional Application No. 61/348,280, filed on May 26, 2010, the entire contents of which are incorporated herein by reference.

FIELD OF THE INVENTION

The present invention relates to liquid mixtures. More specifically, the invention pertains to methods of preparing liquid mixtures of known pH and salt concentration for use in various methods in analytical chemistry, such as liquid chromatography systems.

BACKGROUND OF THE INVENTION

Liquid chromatography is a form of chromatography used frequently in biochemistry and analytical chemistry to separate, identify, and quantify compounds based on their properties such as polarity and their interactions with a stationary phase. Liquid chromatography can be performed using planar or column techniques. In both cases, the system includes a chromatographic device with a stationary phase, a means for moving a mobile phase (solvent carrying compounds of interest) through the device (such as a pump, or gravity), and a detector that creates an electrical signal that identifies a particular compound based on the time of the signal and the amount of the compound based on the intensity of the signal. The detector may also provide other characteristic information (e.g. UV/Vis spectroscopic data for a compound if so equipped). Retention time of a compound in the device varies depending on the strength of the compound's interactions with the stationary and mobile phases, the ratio/composition of the mobile phase that is used, and the flow rate of the mobile phase.

The composition of the mobile phase flowing through the chromatographic device is critical to obtaining the required separation of compounds. For example, in ion exchange chromatography, the pH and/or salt concentration of the mobile phase changes over the course of the separation, to elute different compounds at different times. Prior art systems allowed users to blend multiple solvents to create mobile phases of particular pH and/or salt concentrations. However, in these systems the user was required to know not only the pH and salt concentrations of their particular solvents, but also the pH and salt concentrations that would result from mixing the solvents in various proportions. It would be desirable to have a system and method for automatically calculating and blending the solvents in the desired proportions, to produce a particular pH and/or salt concentration specified by a user, and for varying the proportions of solvents over the course of the elution.

SUMMARY OF THE INVENTION

Accordingly, in one aspect the invention provides a method of preparing a liquid mixture, the mixture comprising one or more acids, one or more bases, one or more salts, and one or more solvents, the method comprising the steps of: i) calculating pH and/or salt concentration at a particular time t from a user-determined gradient function; and ii) based on the values obtained in step (i), calculating percent acid, percent base, percent salt and percent solvent in the liquid mixture at time t.

In additional aspects, the invention also provides a computer program for determining relative proportions in a liquid mixture according to the above algorithm, wherein the proportions are used for controlling a liquid mixture preparation device. Also provided is an eluent preparation device comprising i) a liquid mixture preparation device comprising a mixed liquid outlet port and a plurality of inlet ports connected to component sources of at least one of an acid, a base, a salt, and a solvent, and ii) a mixer control unit arranged to control the relative component proportions supplied through the inlet ports of the liquid mixture preparation device, wherein the mixer control unit i) calculates pH and/or salt concentration at a particular time t from a user-determined gradient function; and ii) based on the values obtained in step (i), calculates percent acid, percent base, percent salt and percent solvent in the liquid mixture at time t.

A liquid chromatography system comprising an eluent preparation device is also provided.

DESCRIPTION OF THE DRAWINGS

The invention is further illustrated by the following drawings in which.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all sub-ranges subsumed therein.

The chromatographic system uses four stock solvents to create the desired pH-salt gradients for an elution, the solvents comprising an acid solution, a base solution, a salt solution and a solvent solution that is typically water, but may contain other additives. In some separations an organic solvent is substituted for the salt. Thus, as used herein, including in the claims, the term "salt" is understood to mean a salt solution, or its substitute, an organic solvent solution.

These four stock solutions are metered in different relative concentrations to generate a given pH-salt concentration condition for the delivered mobile phase at a given point of time.

In an embodiment of the invention, four different types of data are entered by the user into the computer program which controls operation of the chromatography system and specifically delivery of the correct solutions at the pump: 1) a pH-salt gradient table; 2) an empirical pH calibration table (or $pK_a$); 3) molar concentrations of acid, base and salt stock solutions; and 4) the desired acid+base molar concentration that will be delivered to the stationary phase.

A pH look-up table is used by the software to calculate the percentage flow from acid and base lines during the elution.

The look-up table is created by the software either from a user-input $pK_a$ or from a user-input empirical calibration table. The empirical calibration table is created by the user by mixing the 2-4 solutions in known proportions and measuring the pH. The software then uses these input values to calculate the percent acid and base (described further below) at a given time point in the gradient table.

The gradient that is delivered to the stationary phase is determined in the following manner, based on the user-entered information.

A pH-salt gradient table has values for 1) flow rate, 2) pH, 3) change in pH, (referred to herein as a "pH curve"), 4) salt concentration and 5) change in salt concentration (referred to herein as the "salt curve"), for each time t during the course of the separation. Typically, a user will prepare a table having 5 to 6 rows, for times $t_0$ to $t_5$ (or $t_6$). An example of a pH-salt gradient table is shown in Table 1:

TABLE 1

| Time (min) | Flow (mL/min) | pH | pH Curve | Salt Conc. | Salt Curve |
|---|---|---|---|---|---|
| Ink. | 0.5 | 6.8 | ... | 0.05 | ... |
| 10 | 0.5 | 6.8 | 6 | 0.8 | 6 |
| 12 | 0.5 | 6.8 | 6 | 0.8 | 6 |
| 15 | 0.5 | 6.8 | 11 | 0.05 | 11 |

Figure 1:
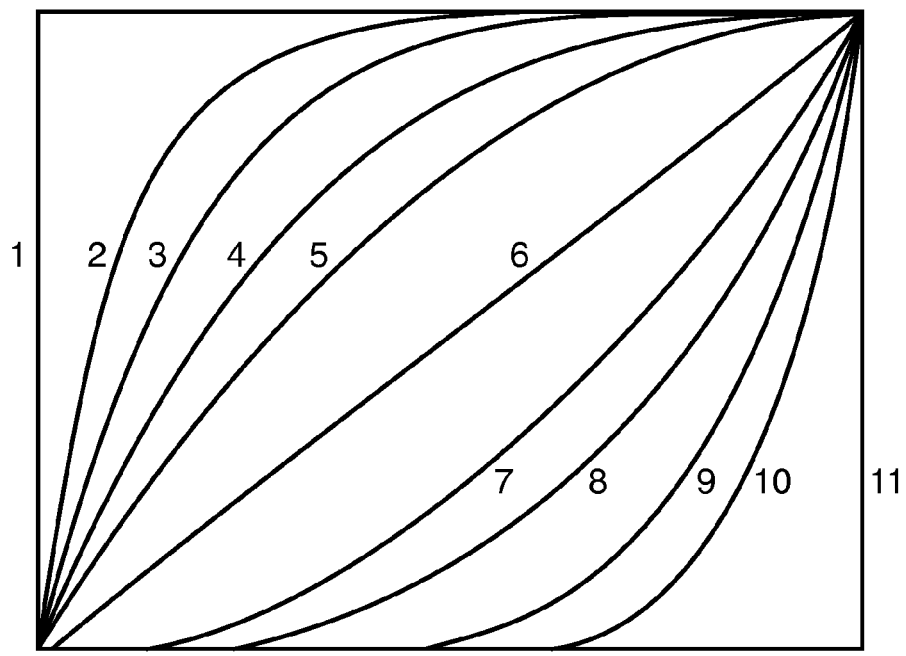
FIG. 1 is a diagram of different curves that are used to change the pH or salt concentration over the course of an elution.

Each time period, for example the time from $t_1$ to $t_2$, is referred to a "time segment". The pH or salt curve determines how the pH or salt concentration will change over that particular time segment. Examples of curves, which can be used to vary both the pH and salt concentration, are depicted in the FIG. 1. The change can be linear, where halfway through the time segment the percentages are halfway between the starting and the ending percentages. The change may also occur more quickly at the beginning of the time segment and more slowly at the end of the segment, a convex curve. The opposite pattern, a concave curve is also possible. The change can also be a step at either the beginning or the end of the segment. The change of pH and salt concentration can be independently varied or held constant from one time segment to another, depending on the needs of the user.

The pH-salt gradient table is prepared by the user based on experimentation and prior experience with particular solvents and analytes of interest, and is within the ability of one skilled in the art of chromatography systems.

The user enters the $pK_a$ from which the look-up table is calculated, or they may enter an empirical calibration from which the pH look-ups are calculated, into the computer program. Optionally, the system can include pre-generated look-up tables for common buffer systems that can be selected by the user. The look-up table can be a one-variable, two-variable or three-variable table; in each, the pH is calculated or measured based on the values of the other variables. A three-variable table will have values for temperature, salt concentration (molar) and base percent (%); a two-variable look-up table will have values for salt concentration (molar) and base percent (%), and a one-variable look-up table has values for base percent. The one-variable table can either be directly entered by the user or calculated by the software based on an input value for the $pK_a$ of the acid used. Typically, a two-variable look-up table may have between 30-60 rows, and a one-variable look-up table will have fewer rows. The two- and three-variable look-up tables are constructed by manually preparing specific mixtures of acid and base buffers, salt and water, and for the three-variable table, temperature. The pH of each mixture at the given conditions is measured and entered into the table.

The user also enters the molar concentrations for each of the acid, base and salt stock solutions that will be combined at the pump in the system.

A final component of the user-entered information is the delivered acid+base concentration. It has been found from experience that a convenient ratio of acid+base percent and salt+solvent percent is about 20% acid+base, and about 80% salt+solvent. However, these numbers are not required, and can be adjusted according to the needs of the user and the analytes being separated.

At a point in time, the pump in the chromatography systems is delivering the specified total flow rate of liquid to the separation column. The software calculates the pH and salt concentration at a particular time t, using the information provided in the gradient table and the look-up table, and a fraction multiplier calculated using the particular pH curve and/or salt concentration curve in the gradient table. Then, for this particular pH and salt concentration, the % base, % acid, % salt and % solvent can be calculated, using interpolation, from values provided in the pH look-up table. These values are sent to the chromatographic system to generate the specific mobile phase conditions for time t.

The method of the invention is further illustrated by way of the following example. Note that an organic solvent can be substituted for a salt in the following calculations, for systems in which organic solvents rather than salts are used.

TABLE 2 pH- Salt Gradient Table (provided by the user)

| time (min) | flow (ml/min) | pH | pH curve | salt conc. (mM) | salt conc. curve |
|---|---|---|---|---|---|
| $T_0 = 0$ | 1.0 ($f_0$) | 5 ($pH_0$) | — | 500 ($sC_0$) | — |
| $T_1 = 10$ | 1.0 ($f_1$) | 6 ($pH_1$) | 6 ($pHC_1$) | 1000 ($sC_1$) | 6 ($sCC_1$) |
| $T_2 = 15$ | 1.0 ($f_2$) | 5 ($pH_2$) | 6 ($pHC_2$) | 500 ($sC_0$) | 6 ($sCC_2$) |
| $T_3 = 16$ | 0 ($f_3$) | 5 | 11 | 500 ($sC_0$) | 11 |

TABLE 3.1

One Variable - pH Look-Up Table
(empirical calibration table)

| base % | pH |
|---|---|
| 0 | 4.0 |
| 5 ($bP_0$) | 5.0 ($pHL_0$) |
| 10 ($bP_1$) | 5.5 ($pHL_1$) |
| 20 | 6.0 |

TABLE 3.2

Two Variables - pH Look-Up Table
(empirical calibration table)

| Salt % | Base % | pH |
|---|---|---|
| 20 ($sPL_0$) | 5 ($bP_0$) | 5.0 ($pHL_0$) |
| 20 ($sPL_0$) | 10 ($bP_1$) | 5.5 ($pHL_1$) |
| 40 ($sPL_1$) | 5 ($bP_0$) | 5.2 ($pHL_2$) |
| 40 ($sPL_1$) | 10 ($bP_1$) | 5.7 ($pHL_3$) |
| ... | ... | ... |

TABLE 3.3

Three Variables - pH Look-Up Table
(empirical calibration table)

| Temp. °C. | Salt % | Base % | pH |
|---|---|---|---|
| 20° C. (Temp$_0$) | 20 (sPL$_0$) | 5 (bP$_0$) | 5.0 (pHL$_0$) |
| 20° C. (Temp$_0$) | 20 (sPL$_0$) | 10 (bP$_1$) | 5.5 (pHL$_1$) |
| 20° C. (Temp$_0$) | 40 (sPL$_1$) | 5 (bP$_0$) | 5.2 (pHL$_2$) |
| 20° C. (Temp$_0$) | 40 (sPL$_1$) | 10 (bP$_1$) | 5.7 (pHL$_3$) |
| 30° C. (Temp$_1$) | 20 (sPL$_0$) | 5 (bP$_0$) | 5.05 (pHL$_4$) |
| 30° C. (Temp$_1$) | 20 (sPL$_0$) | 10 (bP$_1$) | 5.56 (pHL$_5$) |
| 30° C. (Temp$_1$) | 40 (sPL$_1$) | 5 (bP$_0$) | 5.24 (pHL$_6$) |
| 30° C. (Temp$_1$) | 40 (sPL$_1$) | 10 (bP$_1$) | 5.77 (pHL$_7$) |

Molar Concentrations (Provided by the User):
acid concentration: acU=100 mM
base concentration: bcU=100 mM
salt concentration: scU=1000 mM
acid and base concentration (bufferConcentrationU)=20 mM
(bufferConcentrationU≤mM (acU, bcU)
Gradient Function The gradient function is defined by the following set of equations:

$$y = y_s + (y_n - y_s) \times \text{fraction} \quad \text{equation 1}$$

where y is pH and salt concentration (or solvent, if an organic solvent is used), and "fraction" is defined as follows (where values for $t_1$ and $t_0$ are obtained from the pH-salt gradient table, and t is the time of interest, $t_0 \leq t \leq t_1$):

$$\text{Curve 1: fraction} = 1.0 \quad \text{equation 2}$$

$$\text{Curve 2: fraction} = 1 - \left(1 - \frac{t}{t_1 - t_0}\right)^8$$

$$\text{Curve 3: fraction} = 1 - \left(1 - \frac{t}{t_1 - t_0}\right)^5$$

$$\text{Curve 4: fraction} = 1 - \left(1 - \frac{t}{t_1 - t_0}\right)^3$$

$$\text{Curve 5: fraction} = 1 - \left(1 - \frac{t}{t_1 - t_0}\right)^2$$

$$\text{Curve 6: fraction} = \frac{t}{t_1 - t_0}$$

$$\text{Curve 7: fraction} = \left(\frac{t}{t_1 - t_0}\right)^2$$

$$\text{Curve 8: fraction} = \left(\frac{t}{t_1 - t_0}\right)^3$$

$$\text{Curve 9: fraction} = \left(\frac{t}{t_1 - t_0}\right)^5$$

$$\text{Curve 10: fraction} = \left(\frac{t}{t_1 - t_0}\right)^8$$

Curve 11: fraction =
0 if $t < (t_1 - t_0)$ and fraction = 1 if $t = (t_1 - t_0)$.

pH and Salt (or Solvent) Concentration at any Gradient Time t

At any gradient time t, the pH value can be calculated from the gradient function, Equation 1 above, as follows:

From Table 2, the pH-Salt Gradient Table, y=pH, $y_s$=pH$_0$, and $y_n$=pH$_1$, for all values of t where $t_0 \leq t \leq t_1$.

Using curve 6 as an example, the fraction is $$\frac{t}{t_1 - t_0}.$$

$$\text{At time } t, \text{ pH}(t) = \text{pH}_0 + (\text{pH}_1 - \text{pH}_0) \times \frac{t}{t_1 - t_0}. \quad \text{equation 3}$$

Similarly, at time t, and using curve 6 as an example, the salt concentration is calculated as:

$$sC(t) = sC_0 + (sC_1 - sC_0) \times \frac{t}{t_1 - t_0}. \quad \text{equation 4}$$

Calculation of Base Percent
1) Using the one-variable pH Look-up table (Table 3.1), the base percent can be calculated, using interpolation, as follows:

$$\text{BasePercent} = bP_0 + \frac{bP_1 - bP_0}{\text{pHL}_1 - \text{pHL}_0} \times (\text{pH} - \text{pHL}_0) \quad \text{equation 5.1}$$

2) For a given salt percent (sP) and pH, where $sPL_0 < sP < sPL_1$, $pHL_0 < pH < pHL_1$, and
$pHL_2 < pH < pHL_3$, the base percent (%) can be calculated from the values provided by the user in the two-variable pH Look-up table (Table 3.2), using interpolation:

$$bPI_0 = bP_0 + \frac{bP_1 - bP_0}{\text{pHL}_1 - \text{pHL}_0} \times (\text{pH} - \text{pHL}_0) \quad \text{equation 5.2}$$

$$bPI_1 = bP_0 + \frac{bP_1 - bP_0}{\text{pHL}_3 - \text{pHL}_2} \times (\text{pH} - \text{pHL}_2)$$

$$\text{then basePercent} = bPI_0 + \frac{bPI_1 - bPI_0}{sPL_1 - sPL_0} \times (sP - sPL_0)$$

3) For a given temperature (Temp), salt percent (sP) and pH, where

Temp$_0$<Temp<Temp$_1$, $sPL_0 < sP < sPL_1$, $pHL_0 < pH < pHL_1$, $pHL_2 < pH < pHL_3$, $pHL_4 < pH < pHL_5$, $pHL_6 < pH < pHL_7$, the base percent (%) can be calculated from the values provided by the user in the three-variable pH Look-up table (Table 3.3), using interpolation:

$$bPI_0 = bP_0 + \frac{bP_1 - bP_0}{pHL_1 - pHL_0} \times (\text{pH} - \text{pHL}_0) \quad \text{equation 5.3}$$

$$bPI_1 = bP_0 + \frac{bP_1 - bP_0}{pHL_3 - pHL_2} \times (\text{pH} - pHL_2)$$

-continued $$bPI_2 = bP_0 + \frac{bP_1 - bP_0}{pHL_5 - pHL_4} \times (pH - pHL_4)$$

$$bPI_3 = bP_0 + \frac{bP_1 - bP_0}{pHL_7 - pHL_6} \times (pH - pHL_6)$$

$$bPI_4 = bPI_0 + \frac{bPI_1 - bPI_0}{sPL_1 - sPL_0} \times (sP - sPL_0)$$

$$bPI_5 = bPI_2 + \frac{bPI_3 - bPI_2}{sPL_1 - sPL_0} \times (sP - sPL_0)$$

and $$basePercent = bPI_4 + \frac{bPI_5 - bPI_4}{Temp_1 - Temp_0} \times (Temp - Temp_0)$$

Calculation of % A, % B, % C and % D in the Total Mixture (Sent to Gradient Proportioning Valve by Software)
1) Calculation of Salt Percent Max acidPercent×aCU+basePercent×bCU=100%×buffer-ConcentrationU    eq. 5.4.1 acidPercent+basePercent+saltPercent+aqueousPercent=100%    eq. 5.4.2

From equations 5.4.1 and 5.4.2 the following can be derived:

$$acidPercentMax = 100\% \times \frac{bufferConcentrationU}{aCU} \quad \text{eq.5.4.3}$$

$$basePercentMax = 100\% \times \frac{bufferConcentrationU}{bCU} \quad \text{eq.5.44}$$

and saltPercentMax =    eq.5.45
100% − (max of acidPercentMax and basePercentMax)

2) Calculation of Solvent Percentages Sent to Pump:
From equations 5.1, 5.2 or 5.3 basePercent is obtained. From this value, the following can be calculated:

$$acidPercent = \frac{100\% \times bufferConcentrationU - basePercent \times bCU}{aCU} \quad \text{eq.6.1}$$

From Equation 4, saltPercent is calculated as:

$$saltPercent = \frac{sC}{sCU} \times 100\% \quad \text{eq.6.2}$$

if (saltPercent > saltPercentMax) then saltPercent = saltPercentMax aqueousPercent = 100% − acidPercent − basePercent − saltPercent    eq.6.3

The values for acidPercent, basePercent, saltPercent and aqueousPercent can be assigned to solvent A, B, C and D in the pumps.
Calculations for a One-Variable Look-Up Table from $pK_a$
For a given $pK_a$ value $pH_{min} = pK_a - 1$ $pH_{max} = pK_a + 1$ numPH=40 for arrayIndex=0 to arrayIndex=39, $$pH[arrayIndex] = pH_{min} + (pH_{max} - pH_{min}) \times \frac{arrayIndex}{numPH - 1} \quad \text{equation 8}$$

$$basePercent[arrayIndex] = \frac{10^{-pK_a}}{10^{-pK_a} + 10^{-pH[arrayIndex]}} \times 100\% \quad \text{equation 9}$$

So, for example, for a $pK_a=6.8$, $pH_{min}=5.8$, $pH_{max}=6.5$ and numPH=40, a one-variable pH look-up table can be obtained from equations 8 and 9:

TABLE 4

| one-variable pH look-up | |
|---|---|
| Base % | pH |
| 9.09% | 5.8 |
| ... | ... |
| 50% | 6.8 |
| ... | ... |
| 90.9% | 7.8 |

The acid and base components can theoretically be any acid and base, but preferably a weak acid is paired with its conjugate base, or a weak base is paired with its conjugate acid. An example of an acid-base pair is TRIS and TRIS chloride. Other acid-base pair are also suitable and are well known to those skilled in the art.

The salt component preferably is any salt which is neutral to the liquid system, i.e. does not react in the system by any other way than by ionic dissociation. Preferable examples are NaCl or KCl. However, the invention could easily be extended to the use of pH active salts, e.g. ammonium sulphate, and it is considered to be within the knowledge of the person skilled in the art to make the corresponding modifications to the entered variables.

Combinations of acids, combinations of bases, and combinations of salts can also be used.

The solvent component can be any solvent or combination of solvents in which the other components of the liquid mixture are soluble. In one embodiment, the solvent is preferably distilled and/or deionized water. In another embodiment, for example in reverse phase chromatography separations, a water and acetonitrile mixture is preferred.

In other systems, other organic solvents may be used. Typically, when a solvent other than water is used, it preferably is in admixture with water, whereby the pH of the solvent may be taken to be that of the water phase.

In a preferred embodiment, e.g. in a liquid chromatographic system, the calculations are carried out by a data program, implemented from the equations given herein above, governing directly a metering device, such as a pump and valve system, or any other equivalent means of delivering the components to the chromatography device. The program preferably includes the ability to correct for separations carried out at different temperatures, by including temperature in the empirically-derived look-up table (as in Table 3.3). As will be understood by one skilled in the art, the invention is not limited to any particular flow rate, any particular mixing system, or any particular method of generating a flow through a chromatographic device. For example, the method of the invention can be used in both low pressure liquid chromatography (where mixing occurs prior to pumping), and high pressure liquid chromatography, where pumping occurs prior to mixing.

Example

Ion Exchange Separation of Monoclonal Antibody

A commercial preparation of a chimeric monoclonal antibody was analyzed with cation exchange chromatography. The described invention was used to provide different separation buffers to adjust resolution in the separation.

Figure 2:
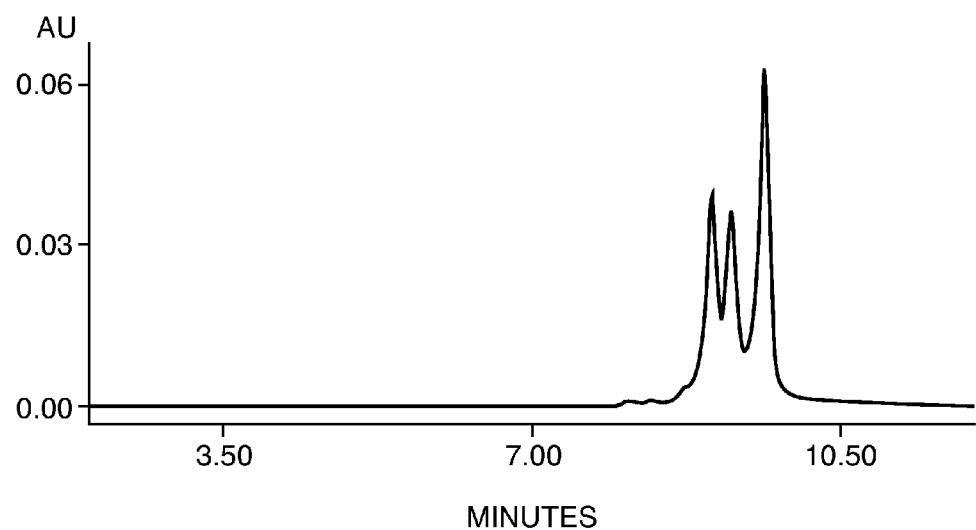
FIG. 2 is a chromatogram showing separation according to the invention as described in the example.

As shown in FIG. 2, the instrument method specified that separation should occur at pH 6.0 with a linear gradient from 0 to 0.5M sodium chloride. Using a specified pK of 6.8, the software calculated that the instrument should blend the mobile phase as 17.26% A and 2.74% B while changing over time from 80% C:0% D to 30% C:50% D.

Figure 3:
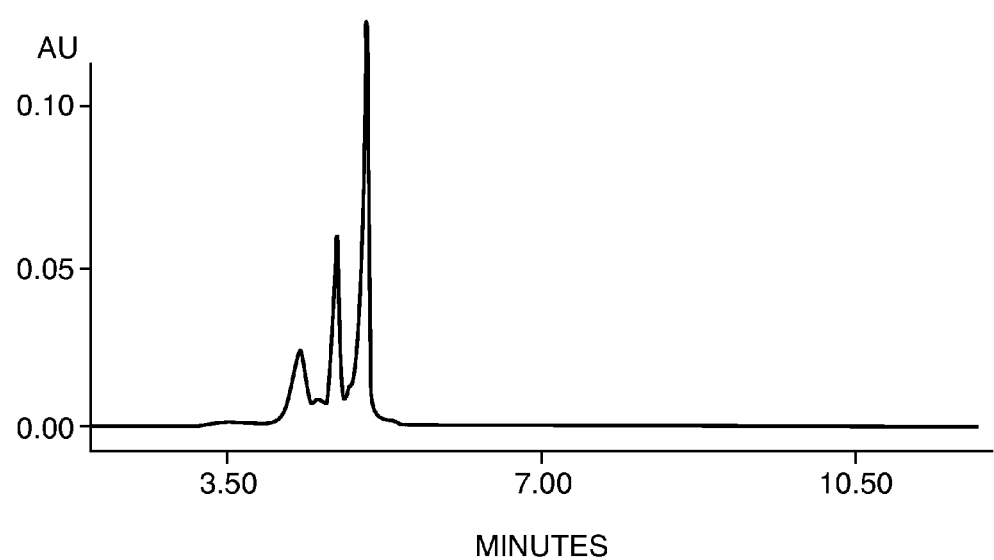
FIG. 3 is a chromatogram showing separation according to the invention as described in the example.

To improve this separation, a second instrument method was created specifying that the same gradient be used at a pH of 6.8. Using the pK of 6.8, the software calculated that the instrument should blend the mobile phase as 10.0% A and 10.0% B while changing over time from 80% C:0% D to 30% C:50% D. The resulting separation is shown in FIG. 3. Retention is lower, and more separated species are apparent.

Experimental Conditions:
Sample: Chimeric Monoclonal Antibody, 4 mg/mL
Injection: 10 uL
Column: Waters Protein-Pak Hi Res SP, 7 mm, 4.6×100 mm
Instrument: Waters ACQUITY UPLC H-Class System with TUV detector at 280 nm
Buffers: A: 0.125M $NaH_2PO_4$
B: 0.125M $Na_2HPO_4$
C: 1.0 M NaCl
D: Water Gradient Table 1

| Time (min) | Flow (mL/min) | pH | pH Curve | Salt Conc. | Salt Curve |
|---|---|---|---|---|---|
| Init. | 1.0 | 6.0 | ... | 0.0 | ... |
| 2 | 1.0 | 6.0 | 6 | 0.0 | 6 |
| 32 | 1.0 | 6.0 | 6 | 0.5 | 6 |
| 32.1 | 1.0 | 6.0 | 6 | 0.0 | 6 |
| 47 | 1.0 | 6.0 | 6 | 0.0 | 6 |

Gradient Table 2

| Time (min) | Flow (mL/min) | pH | pH Curve | Salt Conc. | Salt Curve |
|---|---|---|---|---|---|
| Init. | 1.0 | 6.8 | ... | 0.0 | ... |
| 2 | 1.0 | 6.8 | 6 | 0.0 | 6 |
| 32 | 1.0 | 6.8 | 6 | 0.5 | 6 |
| 32.1 | 1.0 | 6.8 | 6 | 0.0 | 6 |
| 47 | 1.0 | 6.8 | 1 | 0.0 | 6 |

What is claimed is:

1. A method of preparing a liquid mixture, the mixture comprising one or more acids, one or more bases, one or more salts, and one or more solvents, the method comprising the steps of:
   providing a liquid mixture preparation device comprising a mixed liquid outlet port and a plurality of inlet ports connected to component sources of at least one of an acid, a base, a salt, and a solvent;
   providing a mixer control unit arranged to control the relative component proportions supplied through the inlet ports of the liquid mixture preparation device;
   i) receiving by the mixer control unit a pH-salt gradient table containing values for flow rate, pH, pH curve, salt concentration, and salt curve for a plurality of times;
   ii) receiving by the mixer control unit a $pK_a$ of the acid;
   iii) receiving by the mixer control unit concentrations of the component sources of the acid, the base, and the salt;
   iv) receiving by the mixer control unit a desired acid+base concentration for delivery from the mixed liquid outlet port;
   v) calculating by the mixer control unit a pH look-up table containing values for base percent and pH based on the $pK_a$ of the acid;
   vi) calculating by the mixer control unit a pH and/or salt concentration at a particular time t based on values from the pH-salt gradient table and the pH look-up table using a gradient function;
   vii) based on the values obtained in step (vi) and the values from the pH look-up table, calculating by the mixture control unit a percent acid, percent base, percent salt, and percent solvent in the liquid mixture at time t; and
   viii) controlling the relative component proportions supplied through the inlet ports of the liquid mixture preparation device such that the calculated percent acid, percent base, percent salt, and percent solvent are supplied from the mixed liquid outlet port of the liquid mixture preparation device.

2. The method of claim 1, wherein the gradient function comprises a fraction multiplier that provides predetermined changes in pH and/or salt concentration, each being independent of the other, over a time period of interest.

3. The method according to claim 1 or claim 2, wherein the gradient function is based on the following equation:

$$y = y_s + (y_n - y_x) \times \text{fraction} \quad \text{(equation 1)}$$

where y is selected from the group consisting of pH and salt concentration, $y_s$ is the value at time 1 and $y_n$ is the value at time 2.

4. The method according to claim 3, wherein the fraction multiplier is selected from the group consisting of:

1: $\text{fraction} = 1.0$,

2: $\text{fraction} = 1 - \left(1 - \frac{t}{t_1 - t_0}\right)^8$,

3: $\text{fraction} = 1 - \left(1 - \frac{t}{t_1 - t_0}\right)^5$,

4: $\text{fraction} = 1 - \left(1 - \frac{t}{t_1 - t_0}\right)^3$,

5: $\text{fraction} = 1 - \left(1 - \frac{t}{t_1 - t_0}\right)^2$,

6: $\text{fraction} = \frac{t}{t_1 - t_0}$,

7: $\text{fraction} = \left(\frac{t}{t_1 - t_0}\right)^2$,

8: $\text{fraction} = \left(\frac{t}{t_1 - t_0}\right)^3$,

9: $\text{fraction} = \left(\frac{t}{t_1 - t_0}\right)^5$,

10: $\text{fraction} = \left(\frac{t}{t_1 - t_0}\right)^8$ and

11: $\text{fraction} = 0$ if $t < (t_1 - t_0)$ and $\text{fraction} = 1$ if $t = (t - 1 - t_0)$.

5. The method according to claim 1, wherein liquid mixtures are prepared from stock solutions of at least one acid, at least one base, at least one salt, and at least one solvent.

6. The method according to claim 1, further comprising passing the liquid from the mixed liquid outlet port through a stationary phase of a chromatographic device.

* * * * *